United States Patent
Katta

(10) Patent No.: US 9,791,413 B2
(45) Date of Patent: *Oct. 17, 2017

(54) ANALYTE SENSOR AND ANALYTE SENSING METHOD

(71) Applicant: KYOCERA CORPORATION, Kyoto (JP)

(72) Inventor: Hiroshi Katta, Kyoto (JP)

(73) Assignee: KYOCERA CORPORATION, Kyoto (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/894,885

(22) PCT Filed: Mar. 26, 2014

(86) PCT No.: PCT/JP2014/058559
§ 371 (c)(1),
(2) Date: Feb. 29, 2016

(87) PCT Pub. No.: WO2014/192393
PCT Pub. Date: Dec. 4, 2014

(65) Prior Publication Data
US 2016/0195498 A1 Jul. 7, 2016

(30) Foreign Application Priority Data
May 30, 2013 (JP) .................. 2013-113969

(51) Int. Cl.
*G01N 29/02* (2006.01)
*G01N 29/30* (2006.01)
*G01N 29/44* (2006.01)

(52) U.S. Cl.
CPC ........... *G01N 29/022* (2013.01); *G01N 29/30* (2013.01); *G01N 29/44* (2013.01);
(Continued)

(58) Field of Classification Search
CPC .... G01N 29/22; G01N 29/30; G01N 2291/12; G01N 29/44
See application file for complete search history.

(56) References Cited

U.S. PATENT DOCUMENTS 5,478,756 A * 12/1995 Gizeli .................. G01N 29/022
310/311
7,170,213 B2 * 1/2007 Yamanaka ........... G01N 29/022
310/313 A
(Continued)

FOREIGN PATENT DOCUMENTS

JP 7-159381 6/1995
JP 2001-249118 9/2001
(Continued)

OTHER PUBLICATIONS

Hato, I. et al., "Development of Novel SAW Liquid Sensing System with SAW Signal Generator", the IEICE technical report, The Institute of Electronics, Information and Communication Engineers, Feb. 2003, in 6 pages.
(Continued)

*Primary Examiner* — Sam P Siefke
(74) *Attorney, Agent, or Firm* — Duane Morris LLP

(57) ABSTRACT

There are provided an analyte sensor and an analyte sensing method which provide measurements in a wide phase range, a reduction in size, and lowering of current consumption. That is, in an analyte sensor and an analyte sensing method, a detection element which outputs a detection signal in accordance with a change in mass in a detection portion and a reference element which outputs a reference signal in accordance with a change in mass in a reference portion are provided, a phase change value is determined from the detection signal and the reference signal by heterodyne system, and an amount of detection of a target is calculated.

4 Claims, 11 Drawing Sheets

(52) U.S. Cl.
CPC . *G01N 2291/012* (2013.01); *G01N 2291/025* (2013.01); *G01N 2291/0255* (2013.01); *G01N 2291/0256* (2013.01); *G01N 2291/0423* (2013.01)

(56) References Cited

U.S. PATENT DOCUMENTS

| | | | | |
|---|---|---|---|---|
| 8,113,063 B2* | 2/2012 | Nakaso | ................ | G01N 29/022 73/861 |
| 2008/0085212 A1* | 4/2008 | Adams | ................ | G01N 29/036 422/50 |
| 2010/0170345 A1* | 7/2010 | Noguchi | .............. | G01N 29/022 73/646 |
| 2013/0156644 A1* | 6/2013 | Lee | ...................... | G01N 29/022 422/69 |
| 2015/0017735 A1 | 1/2015 | Katta | | |

FOREIGN PATENT DOCUMENTS

| | | |
|---|---|---|
| JP | A 2008-122105 | 5/2008 |
| JP | 5421502 B1 | 2/2014 |
| WO | WO 2009/037977 A1 | 3/2009 |

OTHER PUBLICATIONS

International Search Report for international application No. PCT/JP2013/051887, dated Mar. 12, 2013, in 2 pages.

* cited by examiner

ANALYTE SENSOR AND ANALYTE SENSING METHOD

TECHNICAL FIELD

The present invention relates to an analyte sensor capable of measuring properties of an analyte or a target contained in an analyte, as well as to an analyte sensing method.

BACKGROUND ART

There is known a surface acoustic wave sensor for measuring properties or ingredients of a liquid which is an analyte, by means of a surface acoustic wave device.

The surface acoustic wave sensor, which is constructed of a piezoelectric substrate on which is mounted a detecting section which reacts with a component contained in an analyte sample, detects properties or ingredients of a liquid which is an analyte by measuring electric signals responsive to variations in surface acoustic wave (SAW) propagating through the detecting section (for example, refer to Patent Literature 1).

The SAW sensor disclosed in Patent Literature 1 measures the concentration of an analyte by detecting a phase difference in SAW. A quadrature modulation system is customarily adopted for phase difference measurement from the standpoint of an extended measurable phase range (for example, refer to Non Patent Literature 1).

CITATION LIST

Patent Literature

Patent Literature 1: Japanese Unexamined Patent Publication JP-A 2008-122105

Non Patent Literature

Non Patent Literature 1: "Development of Novel SAW Liquid Sensing System with SAW Signal Generator", the IEICE technical report, The Institute of Electronics, Information and Communication Engineers, February, 2003

SUMMARY OF THE INVENTION

Technical Problem

However, the quadrature modulation system poses the following problems: the number of components constituting the system is so large that system downsizing is difficult; and the number of digital processing steps is so large that current consumption is increased.

In light of this, an analyte sensor which is compact in size and features lower current consumption, and an analyte sensing method have been sought after.

Solution to Problem

An analyte sensor in accordance with the embodiment of the invention comprises: a detection element having a detection portion which undergoes a change in mass in response to adsorption of a target contained in an analyte or reaction with the target, the detection element outputting a detection signal which is an AC signal responsive to the change in mass in the detection portion; a reference element having a reference portion which does not adsorb the target or does not react with the target, the reference element outputting a reference signal which is an AC signal serving as a reference relative to the detection signal; a branching section which branches one of the detection signal and the reference signal into a first signal and a second signal, and branches the other signal of the detection signal and the reference signal into a third signal and a fourth signal; a first computation portion which derives a first measurement signal from the first signal and the third signal by heterodyne system; a second computation portion which derives a second measurement signal from the second signal and the fourth signal by heterodyne system, the second measurement signal being different in a phase-difference from the first measurement signal excluding differences of ±180°; a measurement section which calculates two first candidate phase change values from the first measurement signal and calculates two second candidate phase change values from the second measurement signal, and determines a combination of a first candidate phase change value and a second candidate phase change value that are closest to each other among combinations of the two first candidate phase change values and the two second candidate phase change values, and defines the first candidate phase change value and the second candidate phase change value of the combination as a first phase change value and a second phase change value, respectively; and a selection section which selects a phase change value from the first phase change value and the second phase change value, the phase change value being closer to a reference value in terms of signal output value.

An analyte sensing method in accordance with the embodiment of the invention comprises: an analyte solution supply step of feeding an analyte solution containing an analyte with a target to a detection portion comprising a detection element that undergoes a change in mass in response to adsorption of the target or reaction with the target, and a reference portion comprising a reference element that does not adsorb the target or does not react with the target; a branching step of branching one of a detection signal which is an AC signal responsive to the change in mass in the detection portion outputted from the detection element and a reference signal which is an AC signal based on a mass of the reference portion outputted from the reference element into a first signal and a second signal, and branching the other signal of the detection signal and the reference signal into a third signal and a fourth signal; a first computation step of deriving a first measurement signal from the first signal and the third signal by heterodyne system; a second computation step of deriving a second measurement signal from the second signal and the fourth signal by heterodyne system, the second measurement signal being different in a phase-difference from the first measurement signal excluding differences of ±180°; a measurement step of calculating two first candidate phase change values from the first measurement signal, calculating two second candidate phase change values from the second measurement signal, determining a combination of a first candidate phase change value and a second candidate phase change value that are closest to each other among combinations of the two first candidate phase change values and the two second candidate phase change values, and defining the first candidate phase change value and the second candidate phase change value of the combination as a first phase change value and a second phase change value, respectively; and a selection step of selecting a phase change value from the first measurement signal and the second measurement signal, the phase change value being closer to a reference value in terms of signal output value.

Advantageous Effects of Invention

An analyte sensor and an analyte sensing method in accordance with the embodiment of the invention are capable of measurements in a wide phase range, a reduction in size, and lowering of current consumption.

DETAILED DESCRIPTION

Hereinafter, embodiments of an analyte sensor according to the invention will be described in detail with reference to drawings. In each drawing which will hereafter be described, identical constituent members are identified with the same reference symbols. Moreover, the size of each member, the distance between the members, and so forth are schematically depicted and may therefore be different from the actual measurements.

Moreover, although each side of the analyte sensor may be either an upper side or a lower side, in the following description, for purposes of convenience, an x-y-z rectangular coordinate system is defined, and, words such as an upper surface, a lower surface, etc. are used on the understanding that a positive z direction is an upward direction.

<Analyte Sensor>

First Embodiment (Analyte Sensor 100)

Figure 1:
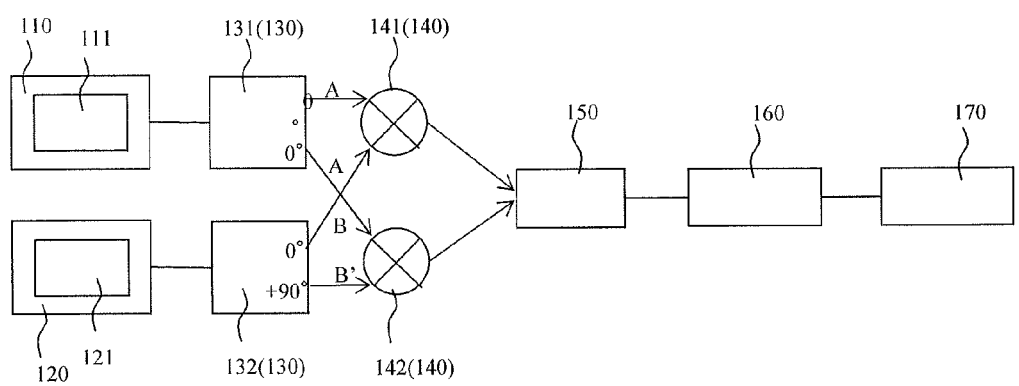
FIG. 1 is a block diagram showing the structure of an analyte sensor in principle in accordance with a first embodiment of the invention.

FIG. 1 is a schematic diagram for explaining the principle of an analyte sensor 100.

As shown in FIG. 1, the analyte sensor 100 comprises: a detection element 110; a reference element 120; a branching section 130; a computation section 140; a measurement section 150; a selection section 160; and a detection amount calculation section 170.

(Detection Element 110)

The detection element 110 includes a detection portion 111 onto which a target present in an analyte is adsorbed, or which undergoes a change in mass in response to a reaction with the target. For example, the detection portion 111 can be implemented by immobilizing a reactive group having such a reactivity as to allow specific target adsorption on a gold (Au) film which is impervious to the influence of the electrical characteristics, such as electrical conductivity, of an analyte. Note that a target does not necessarily have to be adsorbed in itself. For example, a reactive group having such a characteristic as to react only with a target, but not to react with a substance other than a target present in an analyte may be immobilized on a Au film. It is preferable that this Au film is electrically grounded. With this construction, the mass of the detection portion 111 is changed in accordance with the amount of a target.

(Reference Element 120)

The reference element 120 includes a reference portion 121 which does not adsorb a target or does not react with a target. For example, the reference portion 121 does not have such a reactivity as to allow specific adsorption of a target present in an analyte or to cause substitution reaction with a substance contained in an analyte resulting from a conformational change. More specifically, use can be made of a Au film free of immobilization of the aforementioned reactive group, or a component obtained by immobilizing, on a Au film, for example, DNA or RNA which is substantially identical in substance quantity with the aforementioned reactive group, and has a random base sequence. With this construction, the reference portion 121 can be restrained from undergoing a change in mass, depending upon the amount of a target.

Externally input signals are fed to he detection element 110 and the reference element 120. An input signal fed to the detection element 110 passes through the detection portion 111 while undergoing a change in response to a mass change in the detection portion 111, and is then outputted as a detection signal. Similarly, an input signal fed to the reference element 120 passes through the reference portion 121 while undergoing a change in response to a mass change in the reference portion 121, and is then outputted as a reference signal.

The detection signal and the reference signal are each an AC signal, and, the reference signal serves as a signal of reference relative to the detection signal.

(Branching Section 130)

The branching section 130 includes a first branching portion 131 and a second branching portion 132. The first branching portion 131, which is connected to the detection element 110, branches a detection signal responsive to the change in mass in the detection portion 111 comprising the detection element 110 into a first signal and a second signal. The first signal and the second signal are the same in phase. That is, the detection signal is branched into two identical signals A.

The second branching portion 132 branches a reference signal from the reference element 120 into a third signal and a fourth signal. The third signal is the same in phase as the first signal. The fourth signal differs in phase from the first signal excluding differences of 180°. In this embodiment, there is a 90° phase difference. In FIG. 1, the third signal is designated by the symbol B, and the fourth signal is designated by the symbol B'.

Such first and second branching portions 131 and 132 are constructed of a splitter, for example. The second branching portion 132 may be implemented by, after branching a signal line into two in the usual way, making the line length of one of them different from the line length of the other.

(Computation Section 140)

The computation section 140 includes a first computation portion 141 and a second computation portion 142.

The first computation portion 141 derives a first measurement signal from the first signal A and the third signal B by heterodyne system. In this embodiment, the first computation portion 141 obtains a first measurement signal defined by a value obtained by subtracting the third signal B from the first signal A by the heterodyne system.

The second computation portion 142 derives a second measurement signal from the second signal A and the fourth signal B' by the heterodyne system. In this embodiment, the second computation portion 142 obtains a second measurement signal defined by a value obtained by subtracting the fourth signal B' from the second signal A by the heterodyne system.

Such first and second computation portions 141 and 142 are constructed of a mixer and a low-pass filter, for example.

(Measurement Section 150)

The measurement section 150 calculates two first candidate phase change values on the basis of the first measurement signal, and determines one of them as a first phase change value. Likewise, the measurement section 150 calculates two second candidate phase change values on the basis of the second measurement signal, and determines one of them as a second phase change value.

Figure 2:
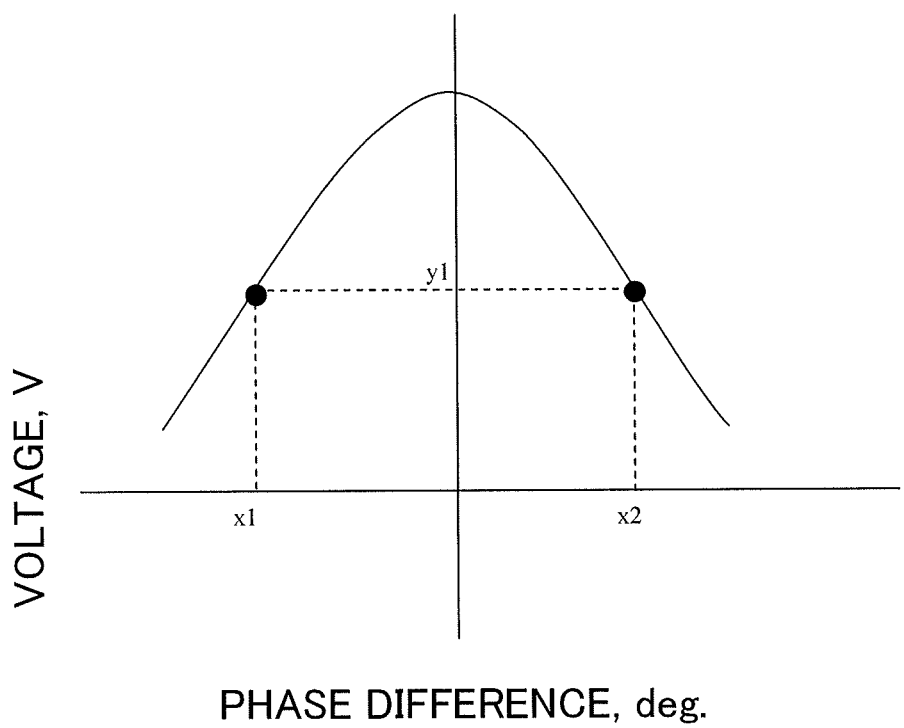
FIG. 2 is a schematic explanatory drawing of a signal processing operation based on heterodyne system.

Since signal processing operation to obtain the first measurement signal and the second measurement signal is performed by heterodyne system, it follows that the first and second measurement signals have a sinusoidal waveform as shown in FIG. 2, wherefore a candidate of a phase change value corresponding to voltage strength (output value) y1 takes on two values x1 and x2. This candidate phase change value is indicative of a phase difference between a detection signal and a reference signal.

Where the first measurement signal and the second measurement signal are concerned, two first candidate phase change values x11 and x21 exist with respect to the first measurement signal, and similarly two second candidate phase change values x12 and x22 exist with respect to the second measurement signal. Among four combinations of a combination of x11 and x12, a combination of x11 and x22, a combination of x21 and x12, and a combination of x21 and x22, candidate phase change values of a combination of values (phase difference values) closest to each other, are defined as the first phase change value of the first measurement signal and the second phase change value of the second measurement signal, respectively. More specifically, a difference between two values of each combination is obtained, and, a combination with the smallest difference is selected. Then, the candidate phase change values constituting the selected combination are defined as the first phase change value of the first measurement signal and the second phase change value of the second measurement signal, respectively. This is based on the following mechanism.

That is, theory holds that one of two first candidate phase change values of the first measurement signal and one of two second candidate phase change values of the second measurement signal are equal. These equal values are correct phase change values (the first phase change value and the second phase change value). However, in the first and second measurement signals obtained by actual measurement, there is a possibility that precisely identical values cannot be obtained due to error. Therefore, a combination with the smallest difference (or equivalently a combination of values closest to each other) is selected to determine the first phase change value and the second phase change value.

In performing signal processing operation by the heterodyne system as has been conventional, there are two candidate phase change values, thus causing difficulty in discrimination between the two values, with a consequent very narrow phase measureable range.

In contrast, according to the present embodiment, as described above, the use of two detection signals (first and second detection signals) makes it possible to determine a phase change value on the basis of candidate phase change values.

(Selection Section 160)

The selection section 160 selects one of two signals composed of the first measurement signal and the second measurement signal as a measurement signal for use in a subsequent process in the detection amount calculation section 170. Likewise, in a case where the selected measurement signal is the first measurement signal, the first phase change value is selected as the phase change value, whereas, in a case where the selected measurement signal is the second measurement signal, the second phase change value is selected as the phase change value.

More specifically, the following procedure is followed: a locus of the first measurement signal and a locus of the second measurement signal are obtained in advance; two signal strengths composed of a strength in positive sign and a strength in negative sign at the intersection points of the first measurement signal and the second measurement signal are determined; and one of the first measurement signal and the second measurement signal that falls in between the strengths in positive and negative signs of two points of intersection is selected as the measurement signal.

FIG. 3(a) is a plot showing the loci of the theoretical values of the first measurement signal and the second measurement signal. For purposes of convenience, the strength of the first measurement signal is represented as V1, the strength of the second measurement signal is represented as V2, and the strengths at the intersection points of the locus of the first measurement signal and the locus of the second measurement signal are represented as Vmax and Vmin, respectively, in order of decreasing level. Moreover, the locus of the first measurement signal is indicated by a broken line, whereas the locus of the second measurement signal is indicated by a solid line. Theory holds that the strengths Vmax and Vmin at the points of intersection are 0.5 times and −0.5 times the maximum levels of the strength V1 and the strength V2, respectively.

Phase values are sectioned, with lines of demarcation drawn at phase values at which the first measurement signal and the second measurement signal exhibit any one of the strengths of two points of intersection. In FIG. 3(a), there are shown Sections 1 to 5. Sections 1 to 4 constitute a cycle to be repeated, and Section 1 and Section 5 are identical. As a measurement signal, the second measurement signal is selected in Section 1, the first measurement signal is selected in Section 2, the second measurement signal is selected in Section 3, the first measurement signal is selected in Section 4, and the second measurement signal is selected in Section 5.

When the first measurement signal is selected as the measurement signal, the first phase change value is defined as a phase change value, and, when the second measurement signal is selected as the measurement signal, the second phase change value is defined as a phase change value.

Or to put it another way, the following conditions are to be fulfilled.

When V1>V2, and V1>Vmax, V2 is selected for the measurement signal.

When V1<V2, and V2>Vmax, V1 is selected for the measurement signal.

When V1<V2, and V1<Vmin, V2 is selected for the measurement signal.

When V1>V2, and V2<Vmin, V1 is selected for the measurement signal.

In a case of V1=V2, any one of them can be selected for the measurement signal. The loci of measurement signals selected are shown in FIG. 3(b).

Selection of a phase change value can be made on the basis of the measurement signal selected under the aforementioned conditions.

(Detection Amount Calculation Section 170)

Next, in the detection amount calculation section 170, the amount of detection of an analyte is determined by calculation using the phase change value selected through the aforestated procedure. The detection amount calculation section 170 is connected to the selection section 160.

With the construction thus far described, an analyte sensor 100 capable of calculating the amount of detection of a target included in an analyte can be provided.

In the analyte sensor of the present embodiment, since signal processing operation is performed by the heterodyne system, the amount of detection of an analyte can be calculated only with the addition of a mixer for deriving a differential between a detection signal and a reference signal. Thus, in contrast to the case of adopting the quadrature modulation system as has been conventional, the analyte sensor does not necessitate complicated signal processing operation, has fewer necessary components, can be made lower in profile, and succeeds in a reduction in current consumption.

Moreover, in a normal heterodyne system, the sign of a phase value cannot be determined, wherefore measurable phases are limited to a range of 0° to 180°. In contrast, according to the analyte sensor 100 of the present embodiment, by making a comparison between the first measurement signal and the second measurement signal in respect of their first and second candidate phase change values, the sign of phase can be determined on the basis of the candidate phase change values, thus allowing estimation of a phase change value. This makes it possible to attain a wider measurable phase range extending from −180° to 180°.

Continuous monitoring of variations in voltage magnitude in the first measurement signal and the second measurement signal allows measurements even in a phase range beyond the limit of 180°.

Moreover, since a normal heterodyne system is based on sinusoidal patterns, the slope of a sine curve decreases with respect to phase differences corresponding to 0° and ±180°, which may result in a decline in sensitivity or an increase of error. In contrast, with the aforestated construction, measurement signals defined by steep slopes are used in the entire phase range excluding the portions defined by the gentle slope. This makes it possible to adjust the rate of change in voltage to be higher relative to the rate of change in phase, and thereby impart high sensitivity to the analyte sensor 100. This is very effective, because, in the analyte sensor, the vicinity of 0° generally corresponds to a rise of a signal change entailed by target detection, wherefore it is desired that this range should be measured with high sensitivity.

Especially in the aforestated case, since the fourth signal differs in phase from the first to third signals by 90°, it follows that, when the first measurement signal poses the lowest sensitivity, the second measurement signal lies in a range that affords highest sensitivity, thus imparting high sensitivity to the analyte sensor 100.

Although the foregoing description deals with the case where the reference signal is branched into the third signal and the fourth signal in a phase-different relation, the detection signal may be branched into the third signal and the fourth signal. Also, although the description deals with the case where the fourth signal differs in phase from the first signal by 90° as the most effective exemplary, a phase difference of other degrees than 90°, except 180°, may be adopted instead.

Moreover, the use of two measurement signals (the first measurement signal and the second measurement signal) as above described enables noise determination. This is based on the following mechanism. While the mixing of noise into a detection signal or a reference signal may take place, it is usually difficult to make a correct judgment about noise. In contrast, according to the analyte sensor 100 of the present embodiment, when measurements are effected precisely, the voltage magnitude of one of the first measurement signal and the second measurement signal takes on a value which falls in between the strengths Vmax and Vmin at the point of intersection, whereas the voltage magnitude of the other takes on a value which lies outside this range. In other words, when both of the first measurement signal and the second measurement signal take on a value which falls within the range or a value which lies outside the range, it can be judged that noise is present. With the capability of correct noise judgment, the analyte sensor 100 enables accurate measurements without incurring the influence of noise.

Thus, there is provided the analyte sensor 100 which is smaller than ever in the number of constituent components and in the number of signal processing steps and yet capable of highly accurate detection in a phase range which is as wide as that for the quadrature modulation system.

(Structure of Analyte Sensor 100A)

Next, referring to FIG. 4, the structure of an analyte sensor 100A which embodies the principle of the analyte sensor 100 as the first embodiment of the invention will be described.

Figure 4:
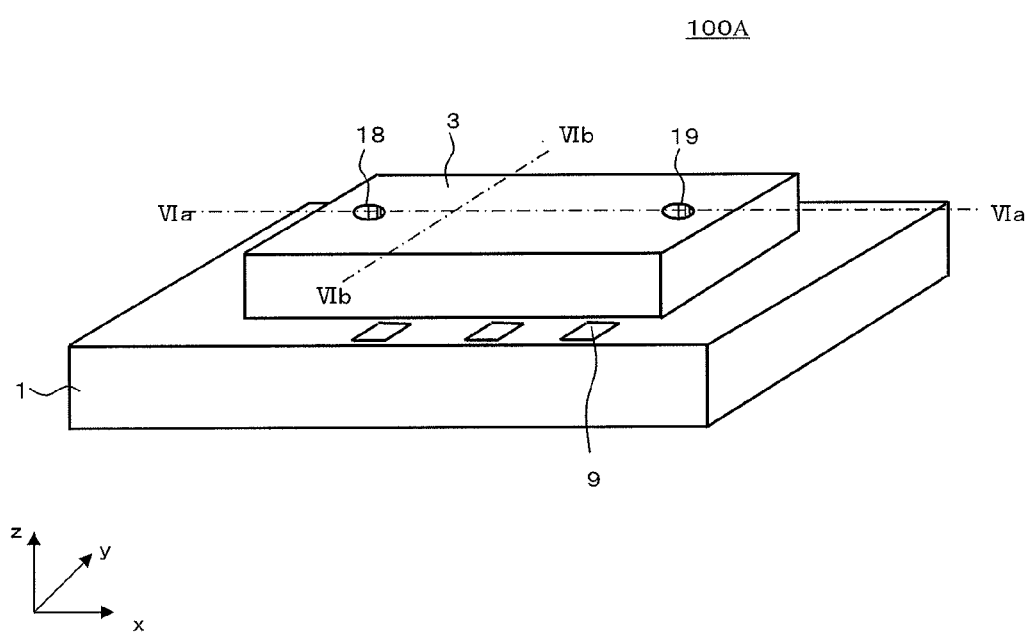
FIG. 4 is a perspective view of the analyte sensor in accordance with the first embodiment of the invention.

As shown in FIG. 4 which is a perspective view, from the standpoint of appearance, the analyte sensor 100A is composed mainly of a piezoelectric substrate 1 and a cover 3. The cover 3 is provided with a first through hole 18 acting as an inlet for an analyte solution, and an air slot or a second through hole 19 acting as an outlet for an analyte solution.

Figure 5:
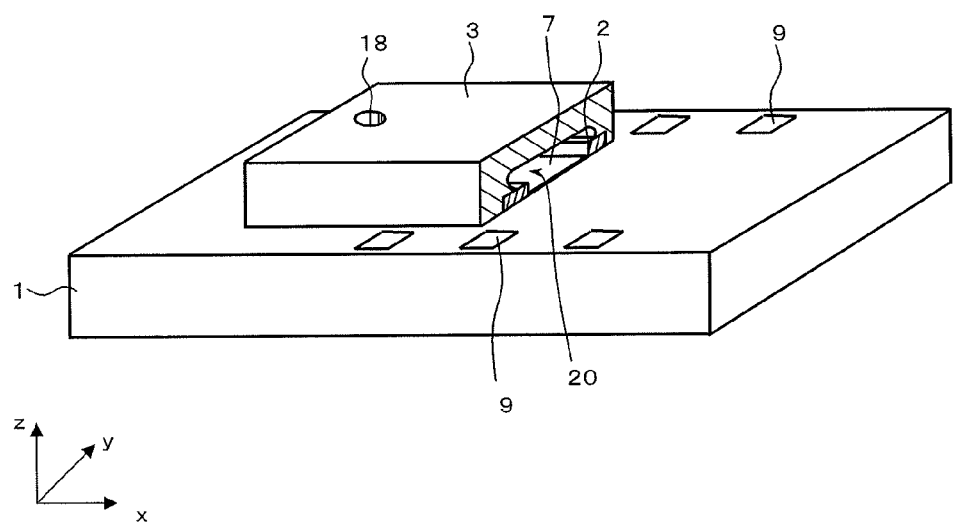
FIG. 5 is a partly cutaway perspective view of the analyte sensor shown in FIG. 4.

FIG. 5 shows a perspective view of the analyte sensor 100A, with one-half of the cover 3 removed. As shown in this drawing, inside the cover 3 a space 20 acting as a flow path for an analyte (solution) is formed. The first through hole 18 is in communication with the space 20. That is, an analyte admitted from the first through hole 18 flows into the space 20.

The analyte solution which has flowed into the space 20 contains a target which reacts with a detection portion made of, for example, a metal film 7 formed on the piezoelectric substrate 1.

The piezoelectric substrate 1 is constructed of a substrate of single crystal having piezoelectric properties such for example as lithium tantalate (LiTaO3) single crystal, lithium niobate (LiNbO3) single crystal, or quartz. The planar shape and dimensions of the piezoelectric substrate 1 are determined appropriately. By way of example, the piezoelectric substrate 1 has a thickness of 0.3 mm to 1 mm.

Figure 6:
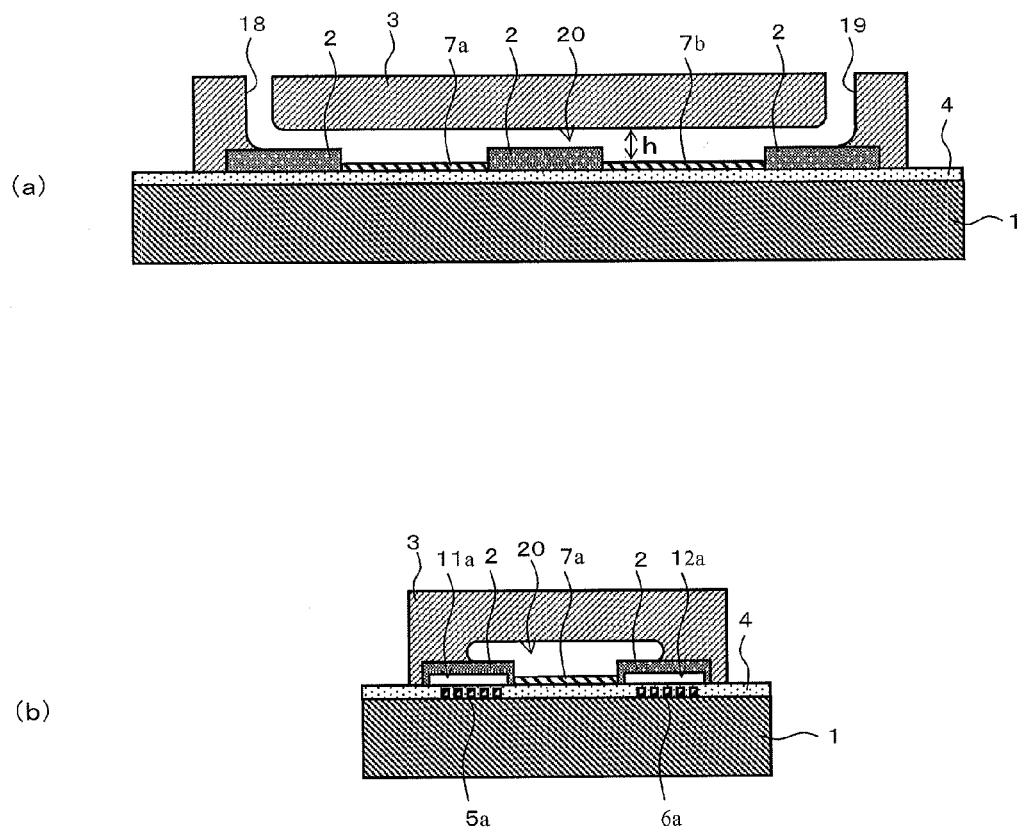
FIG. 6(a) is a sectional view taken along the line VIa-VIa shown in FIG. 4.
FIG. 6(b) is a sectional view taken along the line VIb-VIb shown in FIG. 4.
Figure 7:
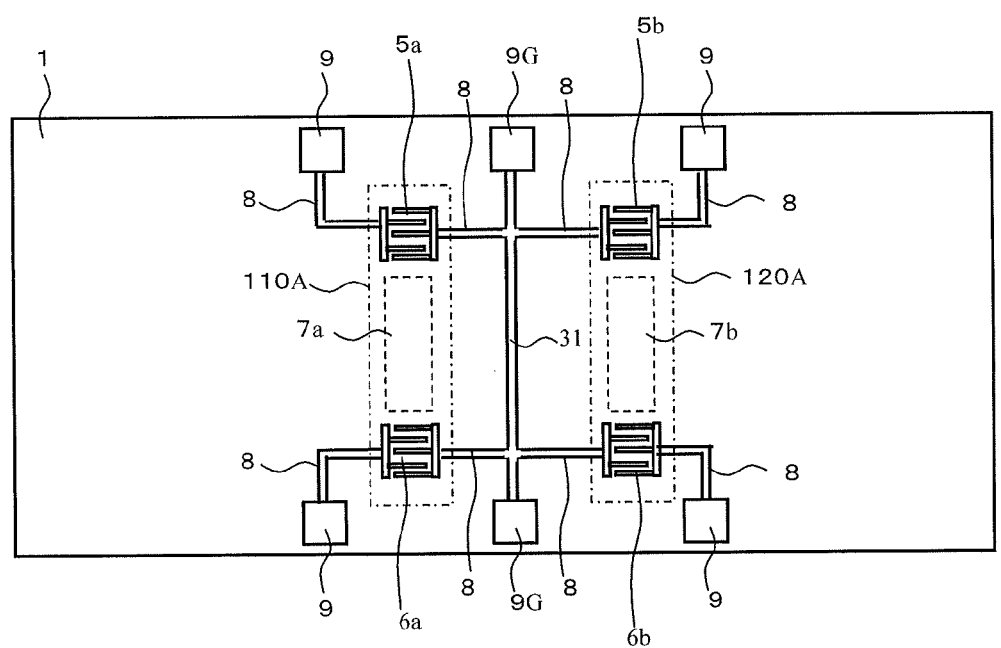
FIG. 7 is a top view of the analyte sensor shown in FIG. 4, with part of the analyte sensor removed.

FIG. 6 shows a sectional view of the analyte sensor 100A. FIG. 6(a) is a sectional view taken along the line VIa-VIa shown in FIG. 4, and FIG. 6(b) is a sectional view taken along the line VIb-VIb shown in FIG. 2. FIG. 7 shows a top view of the piezoelectric substrate 1.

As shown in FIGS. 6 and 7, a first detection IDT electrode 5a, a second detection IDT electrode 6a, a first reference IDT electrode 5b, and a second reference IDT electrode 6b are formed on the upper surface of the piezoelectric substrate 1. The first detection IDT electrode 5a and the first reference IDT electrode 5b are intended for production of predetermined SAW, and the second detection IDT electrode 6a and the second reference IDT electrode 6b are intended for reception of SAW generated by the first detection IDT electrode 5a and SAW generated by the first reference IDT electrode 5b, respectively. The second detection IDT electrode 6a is located on a path over which SAW generated by the first detection IDT electrode 5a propagates so that the second detection IDT electrode 6a can receive SAW generated by the first detection IDT electrode 5a. The first reference IDT electrode 5b and the second reference IDT electrode 6b are located in a similar way.

Since the first reference IDT electrode 5b and the second reference IDT electrode 6b are similar to the first detection IDT electrode 5a and the second detection IDT electrode 6a, respectively, in what follows, the first detection IDT electrode 5a and the second detection IDT electrode 6a will be quoted by way of exemplification.

The first detection IDT electrode 5a and the second detection IDT electrode 6a each comprise a pair of comb-like electrodes (refer to FIG. 7). Each comb-like electrode pair includes two bus bars opposed to each other and a plurality of electrode fingers that extend from one of the bus bars toward the other, and from the other bus bar toward the one bus bar. The comb-like electrode pair is located so that a plurality of the electrode fingers are arranged in an interdigitated pattern. The first detection IDT electrode 5a and the second detection IDT electrode 6a constitute a transversal IDT electrode.

The first detection IDT electrode 5a and the second detection IDT electrode 6a are each connected to a pad 9 via a wiring line 8. A signal is externally inputted to the first detection IDT electrode 5a through the pad 9 and the wiring line 8, and, the signal is externally outputted from the second detection IDT electrode 6a.

The first detection IDT electrode 5a, the second detection IDT electrode 6a, the first reference IDT electrode 5b, the second reference IDT electrode 6b, the wiring line 8, and the pad 9 are made of aluminum (Al) or an alloy of aluminum and copper (Cu), for example. Moreover, the electrodes may have a multilayer structure. In the case of adopting the multilayer structure, for example, the first layer is made of titanium (Ti) or chromium (Cr), and the second layer is made of aluminum or an aluminum alloy.

The first detection IDT electrode 5a, the second detection IDT electrode 6a, the first reference IDT electrode 5b, and the second reference IDT electrode 6b are covered with a protective film 4. The protective film 4 is conducive to the protection of each electrode and wiring from oxidation, for example. The protective film 4 is made of silicon oxide, aluminum oxide, zinc oxide, titanium oxide, silicon nitride, or silicon (Si), for example. In the analyte sensor 100A, silicon dioxide (SiO2) is used for the protective film 4.

The protective film 4 is formed over the entire upper surface of the piezoelectric substrate 1, with the pads 9 left exposed. The first detection IDT electrode 5a and the second detection IDT electrode 6a are covered with the protective film 4. This makes it possible to suppress corrosion of the IDT electrodes.

A thickness of the protective film 4 is 100 nm to 10 μm, for example.

As shown in FIG. 6(b), the first detection IDT electrode 5a is accommodated in a first vibration space 11a, and the second detection IDT electrode 6a is accommodated in a second vibration space 12a. This makes it possible to isolate the first detection IDT electrode 5a and the second detection IDT electrode 6a from outside air and an analyte solution, and thereby protect the first detection IDT electrode 5a and the second detection IDT electrode 6a from a corrosion-inducing substance such as water. Moreover, the provision of the first vibration space 11a and the second vibration space 12a makes it possible to avoid that SAW excitation is seriously hindered in the first detection IDT electrode 5a and the second detection IDT electrode 6a.

The first vibration space 11a and the second vibration space 12a can be formed by joining a plate body 2 having recesses for constituting these vibration spaces to the piezoelectric substrate 1.

Likewise, a first vibration space 11b and a second vibration space 12b are provided for the first reference IDT electrode 5b and the second reference IDT electrode 6b, respectively.

The plate body 2 has, in a region between the recesses constituting the first vibration space 11a and the second vibration space 12a, a penetrating part penetrating therethrough in a thickness direction thereof. This penetrating part is provided to form a metal film 7a on the SAW propagation path. That is, when the plate body 2 joined to the piezoelectric substrate 1 is seen in a plan view, the SAW propagation path for propagating SAW from the first detection IDT electrode 5a to the second detection IDT electrode 6a is, at least partly, exposed from the penetrating part, and, the metal film 7a is formed on this exposed area.

Likewise, the plate body 2 has, in a region between the recesses constituting the first vibration space 11b and the second vibration space 12b, another penetrating part penetrating therethrough in the thickness direction. This penetrating part is provided to form a metal film 7b on the SAW propagation path.

The plate body 2 having such a shape can be formed with use of a photosensitive resist, for example.

The metal film 7a left exposed from the penetrating part of the plate body 2 constitutes a detection portion for detecting an analyte solution. The metal film 7a has a double-layer structure consisting of, for example, chromium and gold deposited in film form on the chromium. An aptamer such for example as a nucleic acid- or peptide-made aptamer is immobilized on the surface of the metal film 7a. Upon contact of an analyte solution with the aptamer-immobilized metal film 7a, a specific target substance contained in the analyte solution is bound to the aptamer adaptable to the target substance. In such a structure, the analyte is bound to the aptamer, and, as adsorption proceeds, the mass of the metal film 7a is monotonically increased. That is, there arises a monotonic increase in mass in response to analyte detection. Note that the mass of the metal film 7a is monotonically increased only during the interval when an analyte is being continuously fed onto the metal film 7a. For example, in the case of feeding a buffer solution subsequently to the feed of the analyte before and after the feed of the analyte solution, even if the analyte passes over the metal film 7a, and a mass reduction is caused by the separation of the analyte from the aptamer, there is no problem.

Moreover, the metal film 7b left exposed from the other penetrating part of the plate body 2 constitutes a reference portion. The metal film 7b has a double-layer structure consisting of, for example, chromium and gold deposited in film form on the chromium. The surface of the metal film 7a is free of aptamer immobilization as done on the metal film 7a, so that the metal film will not exhibit reactivity to an analyte. Moreover, the metal film may be subjected to surface treatment to cause reduced response to an analyte solution for stabilizing purposes.

In measurements of the properties and so forth of an analyte solution by means of SAW, as the first step, a predetermined voltage (signal) is applied, through the pad 9 and the wiring line 8, to the first detection IDT electrode 5a from external measurement equipment. Then, the surface of the piezoelectric substrate 1 is excited in the formed area of the first detection IDT electrode 5a, thus producing SAW having a predetermined frequency. Part of the SAW produced passes through the region between the first detection IDT electrode 5a and the second detection IDT electrode and reaches the second detection IDT electrode 6a. At this time, in the metal film 7a, the aptamer immobilized on the metal film 7a is bound to the specific target substance contained in the analyte, and the weight of the metal film 7 changes correspondingly, which results in variations in the phase characteristics, for example, of the SAW passing under the metal film 7a. Upon the SAW which has undergone such characteristics variations reaching the second detection IDT electrode 6a, a corresponding voltage is developed in the second detection IDT electrode 6a. This voltage is externally outputted through the wiring line 8 and the pad 9 as a detection signal in the form of an AC signal. Thus, the properties and ingredients of the analyte solution can be examined by processing the signal in the branching section 130 and the computation section 140 shown in FIG. 1.

That is, the piezoelectric substrate 1, the metal film 7a acting as the detection portion formed on the piezoelectric substrate 1, the first detection IDT electrode 5a, and the second detection IDT electrode 6a constitute a detection element 110A.

Likewise, the other metal film 7b having no immobilized aptamer is disposed in the same space 20, and, an AC signal outputted from the second reference IDT electrode 6b following the input of a signal from the first reference IDT electrode 5b is defined as a reference signal for use in correction of signal fluctuations caused by environmental variations such as variations in temperature characteristics and humidity.

That is, the piezoelectric substrate 1, the metal film 7b acting as the reference portion formed on the piezoelectric substrate 1, the first reference IDT electrode 5b, and the second reference IDT electrode 6b constitute a reference element 120A.

Although, in this embodiment, one and the same piezoelectric substrate 1 is shared between the detection element 110A and the reference element 120A, a substrate for detection element (first substrate) and a substrate for reference element (second substrate) may be separately provided.

For example, the cover 3 is made of polydimethylsiloxane. The use of polydimethylsiloxane as the constituent material of the cover 3 makes it possible to shape the cover 3 into a desired form. Moreover, with use of polydimethylsiloxane, the ceiling part and the side wall of the cover 3 can be made thick relatively easily. For example, the ceiling part and the side wall of the cover 3 have a thickness of 1 mm to 5 mm.

As shown in FIG. 7, a reference potential line 31 is connected with one of the paired comb-like electrodes constituting each of the first detection IDT electrode 5a, the second detection IDT electrode 6a, the first reference IDT electrode 5b, and the second reference IDT electrode 6b. The reference potential line 31 is connected to a pad 9G so as to serve as a reference potential. Of the paired comb-like electrodes constituting each of the first detection IDT electrode 5a, the second detection IDT electrode 6a, the first reference IDT electrode 5b, and the second reference IDT electrode 6b, the one to be connected to the reference potential is located toward the reference potential line 31. In other words, one of the paired comb-like electrodes that is inwardly located is connected to the reference potential. Such an arrangement makes it possible to suppress signal crosstalk between the detection element 110A and the reference element 120A.

With this construction, it is possible to facilitate the relative layout of the wiring lines 8 for the detection element 110A and the reference element 120A, respectively, as well as to render the wiring lines 8 uniform in length. Thus, the reference signal from the reference element 120A becomes a more accurate signal for reference purposes.

Second Embodiment

Figure 8:
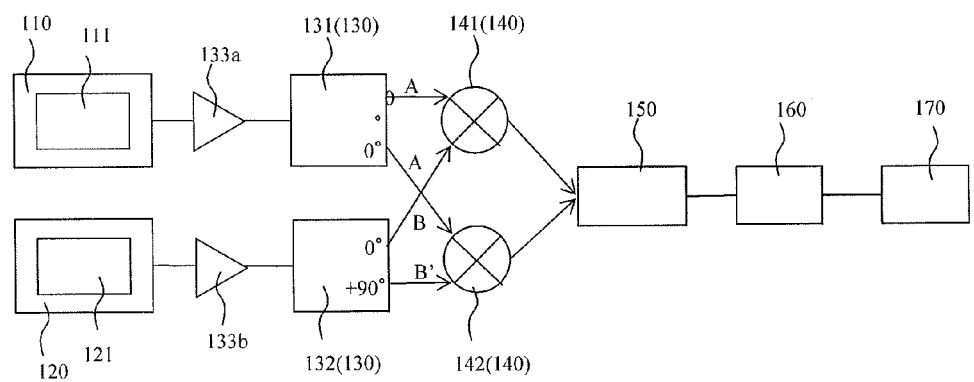
FIG. 8 is a block diagram showing the structure of the analyte sensor in principle in accordance with a second embodiment of the invention.

Next, an analyte sensor 100B in accordance with the second embodiment of the invention will be described with reference to FIG. 8.

The foregoing description about the first embodiment deals with the case where the analyte sensor 100A makes direct use of signals from the detection element 110 and the reference element 120. In contrast, as exemplified in FIG. 8, in the analyte sensor 100B of the second embodiment, a low-noise amplifier 133 may be disposed between the detection element 110 and the first branching portion 131, as well as between the reference element 120 and the second branching portion 132 (a first low-noise amplifier 133a and a second low-noise amplifier 133b).

According to this, high detection accuracy can be attained even under the following circumstances.

In general, in a SAW sensor, high sensitivity can lead to significant variations in amplitude characteristics. Accordingly, where the SAW sensor is designed to have higher sensitivity by making adjustment to, for example, the thickness of the protective film 4, a large loss may occur, thus causing a failure of accurate measurement. In light of this, the interposition of the low-noise amplifier 133 makes it possible to attain high detection accuracy. Meanwhile, a small signal inputted to the computation section 140 may cause an increase in noise with consequent impairment of detection accuracy. In light of this, the interposition of the low-noise amplifier 133 on a path for input to the computation section 140 makes it possible to attain high detection accuracy. The low-noise amplifier 133 should preferably be located at that part of the path for input to the computation section 140 which is closer to each element 110, 120.

Moreover, a large signal inputted to the detection element 110 and the reference element 120 may cause adverse effects such as crosstalk between the signals inputted to the detection element 110 and the reference element 120, respectively, or crosstalk between the input signals and another signal. In light of this, the interposition of the low-noise amplifier 133 on a path for output from the detection element 110 as well as the reference element 120 makes it possible to suppress crosstalk as above described, and thereby attain high detection accuracy. Furthermore, a large signal inputted to the detection element 110 and the reference element 120 may cause external leakage of electromagnetic waves that occurs between the signals inputted to the detection element 110 and the reference element 120, respectively, or between the input signals and another signal. In light of this, the interposition of the low-noise amplifier 133 on the path for output from the detection element 110 as well as the reference element 120 makes it possible to suppress the external leakage of electromagnetic waves as above described, and thereby attain high detection accuracy.

<Analyte Sensing Method>

The following describes an analyte sensing method in accordance with the embodiment of the invention.

(Analyte Solution Supply Step)

At first, there is carried out an analyte solution supply step of feeding an analyte containing a target to the detection portion comprising the detection element that undergoes a change in mass in response to target adsorption or reaction with the target, and the reference portion of the reference element that does not adsorb the target or does not react with the target.

(Branching Step)

Next, one of a detection signal which is an AC signal responsive to the change in mass in the detection portion and a reference signal which is an AC signal from the reference portion is branched into a first signal and a second signal that are the same in phase, and, the other signal of the detection signal and the reference signal is branched into a third signal which is the same in phase as the first signal, and a fourth signal which differs in phase from the first signal excluding differences of 180°.

Although the fourth signal may differ in phase from the first signal by any given degrees excluding differences of ±180°, a ±90° phase difference is desirable.

It is preferable that, prior to the aforestated branching step, the detection signal and the reference signal are each amplified.

(First Computation Step)

Next, a first measurement signal is derived from the first signal and the third signal by heterodyne system.

In effecting computation based on the heterodyne system, either a way to subtract the third signal from the first signal or a way to subtract the first signal from the third signal may be adopted.

(Second Computation Step)

Similarly, a second measurement signal is derived from the second signal and the fourth signal by the heterodyne system.

In effecting computation based on the heterodyne system, as is the case with the aforestated first computation step, either a way to subtract the fourth signal from the second signal or a way to subtract the second signal from the fourth signal may be adopted.

(Measurement Step)

Next, two first candidate phase change values are calculated from the first measurement signal, and two second candidate phase change values are calculated from the second measurement signal. Then, among combinations of the first and second candidate phase change values, a combination of the first candidate phase change value and the second candidate phase change value that are closest to each other is determined, and, the first candidate phase change value and the second candidate phase change value of the determined combination are defined as a first phase change value and a second phase change value, respectively.

(Selection Step)

Next, signal strengths of two points of intersection between the first measurement signal and the second measurement signal are obtained in advance, and, from the first measurement signal and the second measurement signal, a measurement signal that falls in between the strengths of two points of intersection is selected. Similarly, from the first phase change value and the second phase change value, a phase change value corresponding to the measurement signal is selected.

(Detection Amount Calculation Step)

The amount of detected analyte is determined by calculation using the phase change value selected in the selection step.

The analyte detection amount can be measured by following the procedure thus far described.

The invention is not limited to the embodiments as described heretofore, and may therefore be carried into effect in various forms.

Figure 3:
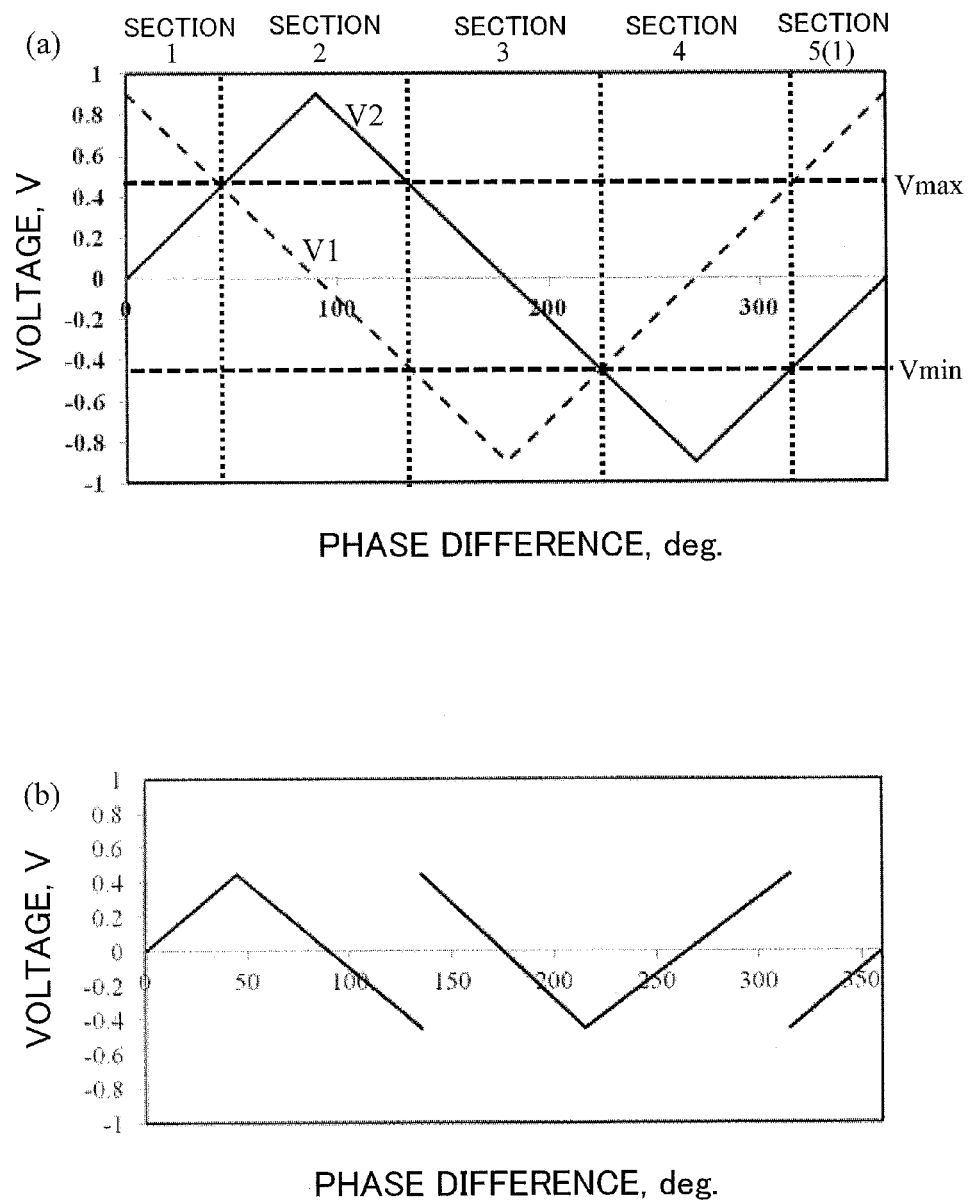
FIG. 3(a) is a plot schematically indicating the loci of first and second measurement signals.
FIG. 3(b) is a plot indicating a locus of a selected measurement signal.

For example, as shown in FIG. 3 for example, the detection sensor of the foregoing embodiments is so designed that signal strengths of two points of intersection between the first measurement signal and the second measurement signal are obtained in advance, and from the first and second measurement signals, a measurement signal that falls in between the strengths of two points of intersection is selected. In the alternative, the sensor may be so designed that from the first phase change value and the second phase change value, a phase change value that is closer to a predetermined reference value in terms of signal output value (for example, V1, V2) is selected. According to this, not only it is possible to provide the same effects as achieved in the foregoing embodiments, but it is also possible to determine a phase change value to be selected on the basis of the predetermined reference value. For example, a midpoint between the aforestated strengths of two points of intersection, or a value of 0 (zero) may be set as the reference value. In the case of adopting the loci of the theoretical values as shown in FIG. 3, the midpoint between the strengths of two points of intersection that serves as the reference value takes on a value of zero. Note that the reference value is not limited to the midpoint between the strengths of two points of intersection, but may be set at any given appropriate value to obtain a measurement signal which affords high sensitivity in consideration of the first measurement signal and the second measurement signal.

Figure 9:
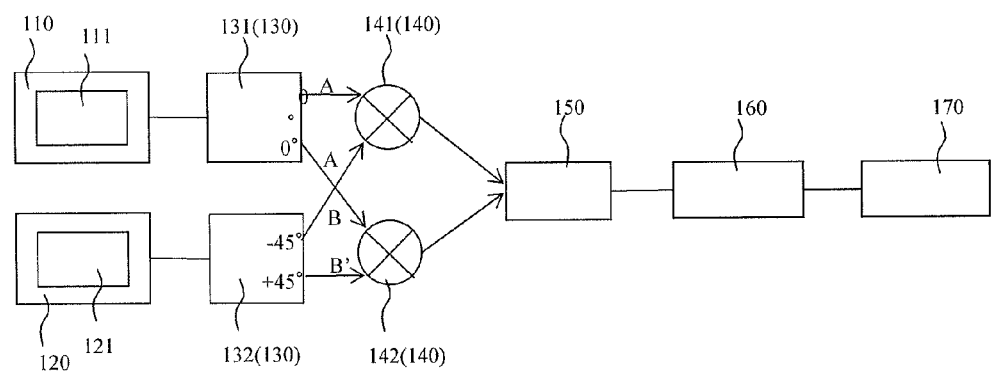
FIG. 9 is a block diagram showing the structure of the analyte sensor in principle in accordance with another embodiment of the invention.

Moreover, as shown in FIGS. 1 to 3 for example, in the detection sensor of the foregoing embodiments, in the second branching portion 132, the third signal is the same in phase as the first signal, and the fourth signal differs in phase from the first signal by 90°. However, the way of setting the phases of the first to fourth signals is not limited to this, and it is sufficient that the phase setting is made so that the first measurement signal and the second measurement signal exhibit a phase difference of a value other than ±180°. For example, in an analyte sensor 100C as exemplified in FIG. 9, the first signal and the second signal are the same in phase, and, the third signal differs in phase from the first signal by −45°, and the fourth signal differs in phase from the first signal by +45°. Also in this case, the same effects as achieved by the analyte sensor of the foregoing embodiments can be provided.

Figure 10:
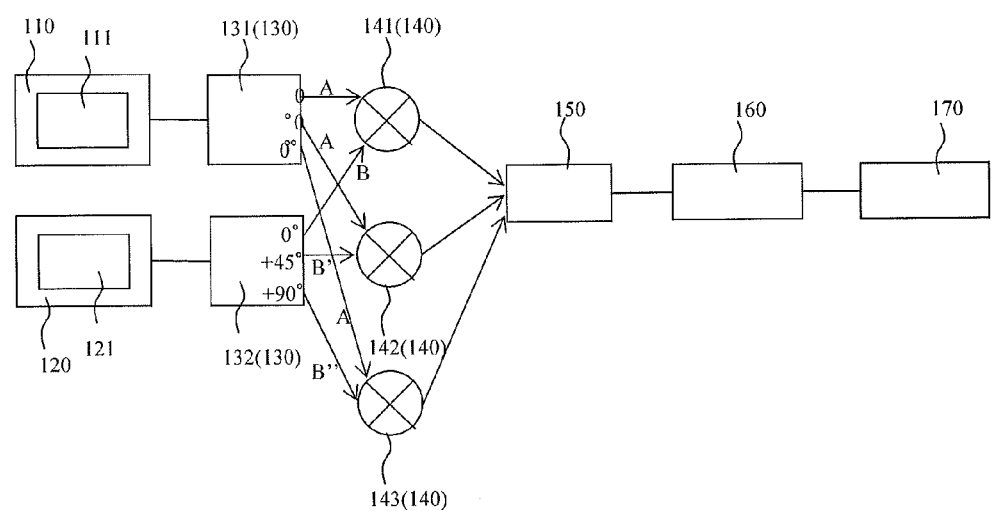
FIG. 10 is a diagram showing the analyte sensor in accordance with another embodiment of the invention.

Moreover, as shown in FIG. 1 for example, in the detection sensor of the foregoing embodiments, the first branching portion 131 and the second branching portion 132 are each adapted to effect signal branching to obtain two signals. In the alternative, each of the first branching portion 131 and the second branching portion 132 may be adapted to effect branching to obtain three or more signals. For example, in an analyte sensor 100D as exemplified in FIG. 10, each of the first branching portion 131 and the second branching portion 132 effects branching to obtain three signals. In this case, two, respectively, of all the signals obtained are used to obtain three measurement signals of varying phase differences by heterodyne system. This makes it possible to provide the same effects as achieved by the aforestated detection sensor. In addition, in this case, even if a range defined by the gentle slope is wide, in other words, even if a range in which measurements can be made with high sensitivity is narrow, in respect of each of the three measurement signals, since a measurement signal corresponding to a range of higher sensitivity can be selected from among the three measurement signals, it is possible to prevent a decline in sensitivity more effectively.

Figure 11:
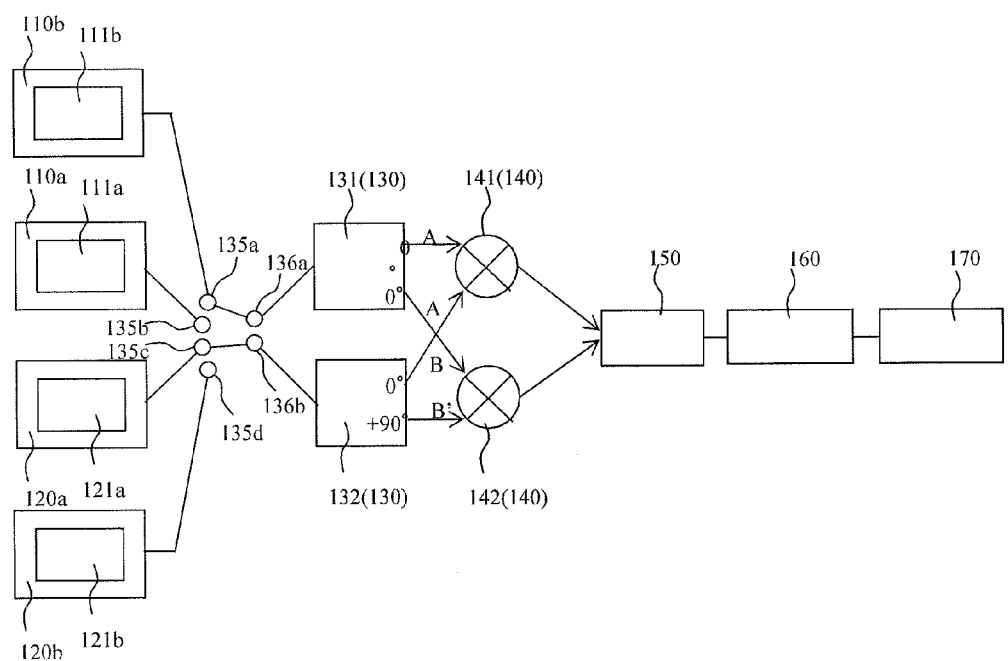
FIG. 11 is a block diagram showing the structure of the analyte sensor in principle in accordance with still another embodiment of the invention.

Moreover, as shown in FIG. 1 for example, the detection sensor of the foregoing embodiments is provided with a single detection element 110 and a single reference element 120, and the single detection element 110 is connected to the first branching portion 131, and the single reference element 120 is connected to the second branching portion 132. In the alternative, as exemplified in FIG. 11, an analyte sensor 100E is provided with two or more detection elements and reference elements, and the two or more detection elements 110a and 110b are connected to the first branching portion 131, and the two or more reference elements 120a and 120b are connected to the second branching portion 132. In this case, the first branching portion 131 is designed to be selectively connectable to one of the two or more detection elements 110a and 110b by a switch 136a, and the second branching portion is designed to be selectively connectable to one of the two or more reference elements 120a and 120b by a switch 136b. This makes it possible to detect two or more to-be-detected targets at one time without the necessity of modifying the configurations of the sections located downstream of the branching section 130, that is; with a single analyte. Moreover, as seen from the configurations of respective switches 135 and 136 shown in FIG. 11, for example, the first branching portion and the second branching portion are each made connectable to either of the detection element and the reference element. In another alternative, there are provided three detection elements and a single reference element. In this case, so long as one of the first branching portion and the second branching portion is made connectable to the reference element, there is no particular limitation as to which one of the three detection elements is connected with the other, and the selection of the detection element is made in accordance with the type of a target to be detected or the number of to-be-detected targets.

Moreover, although the detection sensor of the foregoing embodiments has been illustrated as being designed so that one and the same substrate having piezoelectricity is shared between the detection element 110A and the reference element 120A, an element substrate for the detection element 110A and a second substrate for the reference element 120A may be separately provided. In this case, signal crosstalk between the detection element 110A and the reference element 120A can be suppressed. In such a case, it is advisable to prepare an additional base body for holding the element substrate and the second substrate.

REFERENCE SIGNS LIST

1: Piezoelectric substrate
2: Plate body
3: Cover
4: Protective film
5a: First detection IDT electrode
5b: First reference IDT electrode
6a: Second detection IDT electrode
6b: Second reference IDT electrode
7a, 7b: Metal film
8: Wiring line
9: Pad
11a, 11b: First vibration space
12a, 12b: Second vibration space
20: Space
31: Reference potential line
100, 100A, B, C, D, E: Analyte Sensor
110: Detection element
111: Detection portion
120: Reference element
121: Reference portion
130: Branching section
131: First branching portion
132: Second branching portion
133: Low-noise amplifier
135a, b, c, d: Element-side switch
136a, b: Branching section-side switch
140: Computation section
141: First computation portion
142: Second computation portion
150: Measurement section
160: Selection section
170: Detection amount calculation section.

The invention claimed is:

1. An analyte sensor, comprising:
a detection element having a detection portion which undergoes a change in mass in response to adsorption of a target contained in an analyte or reaction with the target, the detection element outputting a detection signal which is an AC signal responsive to the change in mass in the detection portion;
a reference element having a reference portion which does not adsorb the target or does not react with the target, the reference element outputting a reference signal which is an AC signal serving as a reference relative to the detection signal;
a branching section which branches one of the detection signal and the reference signal into a first signal and a second signal, and branches the other signal of the detection signal and the reference signal into a third signal and a fourth signal;
a first computation portion which derives a first measurement signal from the first signal and the third signal by heterodyne system;
a second computation portion which derives a second measurement signal from the second signal and the fourth signal by heterodyne system, the second measurement signal being different in a phase-difference from the first measurement signal excluding differences of ±180°;
a measurement section which calculates two first candidate phase change values from the first measurement signal and calculates two second candidate phase change values from the second measurement signal, and
determines a combination of a first candidate phase change value and a second candidate phase change value that are closest to each other among combinations of the two first candidate phase change values and the two second candidate phase change values, and defines the first candidate phase change value and the second candidate phase change value of the combination as a first phase change value and a second phase change value, respectively; and a selection section which selects a phase change value from the first phase change value and the second phase change value, the phase change value being closer to a reference value in terms of signal output value.

2. The analyte sensor according to claim 1, wherein the detection element comprises a first substrate having piezoelectricity, and the detection portion, a first detection IDT electrode for producing an elastic wave toward the detection portion and a second detection IDT electrode for receiving the elastic wave which passed through the detection portion that are each located on the first substrate, wherein the reference element comprises a second substrate having piezoelectricity, and the reference portion, a first reference IDT electrode for producing an elastic wave toward the reference portion and a second reference IDT electrode for receiving the elastic wave which passed through the reference portion that are each located on the second substrate, wherein the detection signal is an AC signal which the second detection IDT electrode receives the elastic wave which passed through the detection portion, and wherein the reference signal is an AC signal which the second reference IDT electrode receives the elastic wave which passed through the reference portion.

3. The analyte sensor according to claim 1, further comprising:

a first low-noise amplifier located between the detection element and the branching section, the first low-noise amplifier amplifying the detection signal from the detection element; and a second low-noise amplifier located between the reference element and the branching section, the second low-noise amplifier amplifying the reference signal from the reference element.

4. An analyte sensing method, comprising:

an analyte solution supply step of feeding an analyte solution containing an analyte with a target to a detection portion comprising a detection element that undergoes a change in mass in response to adsorption of the target or reaction with the target, and a reference portion comprising a reference element that does not adsorb the target or does not react with the target;

a branching step of branching one of a detection signal which is an AC signal responsive to the change in mass in the detection portion outputted from the detection element and a reference signal which is an AC signal based on a mass of the reference portion outputted from the reference element into a first signal and a second signal, and branching the other signal of the detection signal and the reference signal into a third signal and a fourth signal;

a first computation step of deriving a first measurement signal from the first signal and the third signal by heterodyne system;

a second computation step of deriving a second measurement signal from the second signal and the fourth signal by heterodyne system, the second measurement signal being different in a phase-difference from the first measurement signal excluding differences of ±180°;

a measurement step of calculating two first candidate phase change values from the first measurement signal, calculating two second candidate phase change values from the second measurement signal, determining a combination of a first candidate phase change value and a second candidate phase change value that are closest to each other among combinations of the two first candidate phase change values and the two second candidate phase change values, and defining the first candidate phase change value and the second candidate phase change value of the combination as a first phase change value and a second phase change value, respectively; and a selection step of selecting a phase change value from the first measurement signal and the second measurement signal, the phase change value being closer to a reference value in terms of signal output value.

* * * * *